(12) United States Patent
Twydell

(10) Patent No.: US 7,351,432 B2
(45) Date of Patent: Apr. 1, 2008

(54) COMPOSITIONS CONTAINING SACCHARIDE AND HYDROPHOBIC SILICA

(75) Inventor: Roland Twydell, Widnes (GB)

(73) Assignee: Sorox Limited (GB)

( * ) Notice: Subject to any disclaimer, the term of this patent is extended or adjusted under 35 U.S.C. 154(b) by 422 days.

(21) Appl. No.: 10/496,345

(22) PCT Filed: Nov. 20, 2002

(86) PCT No.: PCT/GB02/05235

§ 371 (c)(1),
(2), (4) Date: May 21, 2004

(87) PCT Pub. No.: WO03/004152

PCT Pub. Date: Jun. 5, 2003

(65) Prior Publication Data

US 2004/0259836 A1   Dec. 23, 2004

(30) Foreign Application Priority Data

Nov. 24, 2001   (GB) ................................. 0128210.2

(51) Int. Cl.
*A61K 9/16* (2006.01)
*A61K 9/14* (2006.01)
*A61K 33/00* (2006.01)

(52) U.S. Cl. ...................... 424/490; 424/489; 424/493; 424/724

(58) Field of Classification Search ................ 424/489, 424/405, 417, 490, 493, 724; 514/23, 53, 514/54, 63
See application file for complete search history.

(56) References Cited

U.S. PATENT DOCUMENTS 5,122,518 A   6/1992   Vbra
6,821,942 B2 *  11/2004   Sebillotte-Amaud et al. .............. 510/466

FOREIGN PATENT DOCUMENTS

| DE | 197 49 683 | 5/1999 |
| DE | 198 19 856 | 11/1999 |
| EP | 0 855 177 | 7/1998 |
| WO | WO 01/35744 | 5/2001 |
| WO | WO 01/80645 | 11/2001 |

OTHER PUBLICATIONS

International Search Report for Application No. PCT/GB02/05235 dated Mar. 4, 2003.
International Preliminary Examination Report for Application No. PCT/GB02/05235 dated Mar. 4, 2004.

* cited by examiner

*Primary Examiner*—Johann R. Richter
*Assistant Examiner*—Konata M. George
(74) *Attorney, Agent, or Firm*—Cantor Colburn LLP

(57) ABSTRACT

A particulate composition comprises from 40 to 80% by weight of a water-soluble saccharide, from 1.5 to 10% by weight of a finely particulate amorphous hydrophobic silica having a surface area in the range of from 80 to 300 $m^2/g$ and water. The composition is in the form of fine particles of an aqueous solution of the water-soluble saccharide, the surfaces of which fine particles of aqueous solution are coated with a coating of the finely particulate amorphous hydrophic silica.

The composition, which may additionally contain one or more biocidally-active materials, can be applied through conventional dust applicator equipment for the treatment of pests.

28 Claims, No Drawings

COMPOSITIONS CONTAINING SACCHARIDE AND HYDROPHOBIC SILICA

The present invention relates to compositions containing saccharide and hydrophobic silica. More particularly, it relates to compositions comprising an aqueous solution of a water-soluble saccharide and finely divided amorphous hydrophobic silica, to a method of making such compositions and to the use of such compositions.

Aqueous dispersions of silica can be prepared into a state known generally in the prior art as "dry water". In fact, "dry water" is known in two forms. The first can be produced by absorbing aqueous liquids onto hydrophilic material to form a material which exists as free-flowing powder or granules. The second form can be produced by coating finely divided aqueous liquids with powdered hydrophobic material, such as metal oxides. Each liquid particle in the second form of dry water is separated from the next by a hydrophobic metal oxide coating and by air spaces. Very high speeds of, for example, over 6000 rpm, and mixing times of 15 minutes are typically required. The second form is, however, thermodynamically unstable and, when produced, tends to break down after a relatively short period of time.

A dry water composition containing pyrogenically-produced hydrophobic silica is disclosed in U.S. Pat. No. 5,122,518 as being useful for controlling insects and other pests. This dry water composition, however, is unstable and cannot be stored for long periods of time. Also, when this prior art composition is applied using conventional spraying apparatus, it causes blocking of the nozzles of the apparatus and cannot be sprayed over distances comparable to those achieved using a sprayable liquid.

A composition comprising storage-stable aerated gel is described in WO 01/35744. This composition is in the form of fine particles of an aqueous gel containing water and a gelling agent, the surfaces of which fine particles are covered with a coating of finely particulate hydrophobic silica.

The present invention is based on the discovery that storage-stable particulate compositions can be produced using particles of an aqueous solution of a water-soluble saccharide and finely particulate amorphous hydrophobic silica.

The present invention provides a particulate composition comprising from 40 to 80% by weight of a water-soluble saccharide, from 1.5 to 10% by weight of a finely particulate amorphous hydrophobic silica having a surface area in the range of from 80 to 300 $m^2/g$ and water which composition is in the form of fine particles of an aqueous solution of the water-soluble saccharide the surfaces of which fine particles of aqueous solution are coated with a coating of the finely particulate amorphous hydrophobic silica.

The composition of the invention is typically in powder form, more typically in the form of a free-flowing powder.

The present invention also provides a process for producing a particulate composition which comprises the step of mixing from 1.5 to 10% by weight of a finely particulate amorphous hydrophobic silica having a surface area in the range of from 80 to 300 $m^2/g$, from 40 to 80% by weight of a water-soluble saccharide and water whereby fine discrete particles of an aqueous solution of the saccharide become coated on their surfaces by a coating of the amorphous hydrophobic silica particles.

We have found that the particulate compositions of the invention are dry to the touch until direct pressure is exerted whereupon the composition becomes transformed into a sticky cream or paste-like material. The properties of the composition of the present invention are such that it can be applied through conventional dust applicator equipment, yet when applied by such onto a solid target the force of the impact causes part of the composition to transform to a sticky cream or paste-like material which adheres to the target.

Where the words "comprises" and "comprising" are used herein, it is intended that these may have the meanings "includes" and "including", respectively, to the extent that the presence of one or more other materials in respect of a composition, or one or more other process steps, in respect of a process, is not excluded.

The composition of the invention comprises a finely particulate amorphous hydrophobic silica having a surface area in the range of from 80 to 300 $m^2/g$. By the term "finely particulate", as applied to the amorphous hydrophobic silica, it is meant that the silica will typically have an average particle size of less than 40 μm. The silica used is one that has been rendered hydrophobic by surface treatment using one or more organosilicon compounds to produce, on the silicon dioxide surface, hydrophobicizing organosilicon groups such as silicone groups, siloxane groups or silyl groups. The technique of hydrophobicizing silica in this way is well-known and such hydrophobicized silica is available commercially. We have found that good results are obtained using amorphous hydrophobic silica having a surface area within the range of 80 to 300 $m^2/g$ marketed under the brand name CAB-O-SIL ("CAB-O-SIL" is a trade mark of Cabot Corporation). Examples of such hydrophobic silicas include CAB-O-SIL TS720 and CAB-O-SIL TS530. However, other silicas that have been surface treated to produce hydrophobicizing silicone, siloxane or silyl groups on the silica surface may also be used in the present invention if they have a surface area within the range of from 80 to 300 $m^2/g$. The silica will be used in an amount of from 1.5 to 10% by weight, based on the total weight of the composition. The use of the silica in an amount less than 1.5% by weight results in the production of a particulate material having poor stability. The use of the silica in an amount which is greater than 10% by weight tends to produce a particulate material which is excessively dusty. Preferably, the content of the amorphous hydrophobic silica in the composition is in the range of from 2 to 4% by weight. Increasing the silica content of the composition at the expense of water produces a powder of lower bulk density.

The composition comprises at least one water-soluble saccharide. Typically, this will be a monosaccharide, a disaccharide or an oligosaccharide. Higher saccharides have a tendency to give products which are less stable or which are not particulate. Examples of water-soluble saccharides that may be used in the present invention include but are not limited to dextrose, sucrose, lactose, d-galactose, d-mannitol, maltose, d-raffinose and trehalose. Preferably, the saccharide is sucrose in view of the fact that very good results are obtained by its use and also in view of its relatively low cost. The saccharide will be present in the composition of the invention in an amount in the range of from 40 to 80% by weight based on the total weight of the composition. Preferably, the amount of saccharide will be from 50 to 70% by weight. Any granular form of the saccharide may be used to produce the aqueous solution. According to a preferred embodiment, the aqueous solution of the saccharide will be preformed before admixture with the amorphous hydrophobic silica to give the composition of the present invention. Thus, it is within the scope of the invention to use, as the source of the saccharide and at least part of the water, in the composition a saccharide in the form of an aqueous syrup.

In this respect, we have achieved good results using, as the source of the saccharide and at least part of the water required in the composition, a sucrose syrup such as Golden Syrup (also known as cane syrup). Golden syrup comprises 25 to 30% sucrose and about 50% of inverted sugars. In the case where a saccharide syrup is used in the present invention, it may be necessary to add additional water to the mixture of syrup and hydrophobic silica to facilitate the production of the composition of the invention.

Water used in the preparation of the composition of the invention will typically be tap water, although purified grades may be appropriate for some applications. The water will normally be used at ambient temperature since there appears to be no advantage in using heated water or cooled water in the performance of the invention. It may, however, be appropriate in some cases to facilitate the dissolution of a solid saccharide by raising the temperature of the water used above ambient temperature.

We have found that compositions according to the invention have biocidal activity against pests, such as insects, mites and lice in the absence of any added biocidally-active material. Although we do not wish to be bound by theory, we believe that the composition is effective against such pests because of the tendency of the composition to stick to the body of the pest. In the case of mites, the composition can adhere to their legs and can render them immobile. The amorphous hydrophobic silica in the composition also has insecticidal activity since it physically removes epicuticular wax from the insect resulting in the loss of hydrostatic stability in the insect. However, it is within the scope of the invention to incorporate, into the composition, one or more biocidally-active compounds to extend the spectrum of biocidal activity that can be obtained, depending on the choice of biocidally-active compounds used. The biocidally-active compound may, for instance, be selected from one or more rodenticides, insecticides and acaricides. The biocidally-active compound may be hydrophilic or hydrophobic. Examples of such biocidally-active compounds include, but are not limited to, rodenticides of the coumarin type, such as difenacoum, and insecticides such as boric acid and pyrethroids, such as cypermethrin and d-phenothrin.

The amount of a biocidally-active compound, if used, in the composition of the invention may be in the range of from 0.004 to 20% by weight based on the total weight of the composition. The inclusion level will, of course, depend on the potency of the biocide being used and the desired biological performance of the composition. Typically, the biocide will be used in an amount to give a final biocide content in the composition in the range of from 0.005 to 10% by weight of the composition. The composition may additionally contain one or more compounds which stabilise the biocide or act as an adjuvant for the biocide. Also, other additives may be incorporated into the composition if desired, for example flavorants, perfumes, attractants, stabilisers and detergents.

The process for producing the composition of the invention involves mixing the finely particulate amorphous hydrophobic silica with the water-soluble saccharide and water. Typically mixing is carried out for a few minutes, for example 2 to 5 minutes. High shear conditions, i.e. conditions that cause the aqueous phase to be finely fragmented into minute droplets which then become dispersed within the finely particulate hydrophobic silica such that the surfaces of the minute droplets of the aqueous phase become coated with the hydrophobic silica particles are preferred for lower viscosity compositions. The term "high shear" is, of course, well-known to the person skilled in the art of mixing or blending and whether or not a particular mixing apparatus is capable of mixing aqueous compositions under high shear conditions will be known to one skilled in the art. This may be achieved by using standard high speed mixers, typically using a mixing speed of at least 1500 rpm and generally from 2000 to 6000 rpm. When a hydrophilic biocide is used, we have found that it is preferable to dissolve the biocide into the water and then to mix the solution containing the saccharide and the biocide with the hydrophobic silica to partially disperse the silica into the solution. By incorporating the biocide in this way a homogenous distribution of the biocide throughout the eventual composition can be obtained. However, when a hydrophobic biocide is used we prefer to mix the water, the saccharide, the hydrophobic silica and the hydrophobic biocide together under high shear conditions to partially disperse the silica with the biocide and the saccharide solution. If the biocide is, itself, a solid material, then it is preferred to add this as a solution in a minimum amount of an organic solvent with the other ingredients in order to facilitate the eventual production of a composition having a homogenous distribution of the biocide. Alternatively, a finely divided solid biocide may be directly dispersed in the composition with adequate mixing.

In the case where the water-soluble saccharide is provided by means of a high viscosity syrup adequate mixing of the various components of the composition can be achieved with low shear mixers.

The compositions of the present invention, by choice of one or more appropriate biocides, can be tailored to have activity against a variety of pests. For instance, the product composition can be used as a rodenticidal contact formulation by incorporating a rodenticide such as a difenacoum into the composition. Ant bait formulations can be obtained by using, as the biocide, an effective amount of boric acid. According to a preferred embodiment, the composition of the invention contains as biocide, an insecticide which is effective for the control of wasp nests, e.g. nests of the common wasp, *Vespula vulgaris* and the tree wasp, *Dolichovespula sylvestris*. An example of a wasp nest control formulation comprises a composition of the invention containing, as biocide, the insecticide d-phenothrin in an effective amount.

The process of the invention results in the formation of a fine, free-flowing powder composition comprising finely-divided particles of an aqueous sugar solution, each particle of solution being coated by amorphous, hydrophobic silica. The powder is generally dry to touch until direct pressure is applied on it whereupon it becomes a sticky cream or paste. The pressure/adhesive properties enables the powder to adhere well to substrates to which it is forcibly applied. The powder formed according to the process of the invention can be applied through conventional pest control dust applicators such as, for example, BIRCHMEIR DR5™, DUST KING™, B&G MINI DUSTER™, DUST STICK™, CENTRO BULB™ and STIHL™ motorised mistblower/duster. However, unlike conventional pesticidal dusts, the composition of the invention is not sensitive to high humidity or compaction. In addition, the powder gives superior adhesion to substrates compared to conventional pesticidal dusts, primarily due to its impact/adhesion characteristics.

The invention will now be illustrated by the following examples in which all concentrations are given in % m/m.

EXAMPLES

Example 1

Cold tap water (31%), sucrose (66%) and CAB-O-SIL TS720 (3%) were mixed together in an IKA RE166 high speed mixer having a radial flow toothed disk mixer head for 3 minutes. The resultant powder was fine and free-flowing.

The powder formed was stored for 18 months at ambient temperature without any discernible change in physical characteristics.

Example 2

Cold tap water (32%), sucrose (66%) and CAB-O-SIL TS720 (2%) were mixed together in an IKA RE166 high speed mixer having a radial flow toothed disk mixer head for 3 minutes. The resultant powder was coarser and wetter than that formed in Example 1 and had slightly poorer flow characteristics.

Example 3

Cold tap water (33%), sucrose (66%) and CAB-O-SIL TS720 (1%) were mixed together in an IKA RE166 high speed mixer having a radial flow toothed disk mixer head for 3 minutes. The resultant product was not a powder, rather it was a pulverent liquid with poor stability.

Example 4

In this example, a different type of silica from that used in Examples 1 to 3 was used.

Cold tap water (35.6%), sucrose (60.3%) and CAB-O-SIL TS530 (4.1%) were mixed together in an IKA RE166 high speed mixer having a radial flow toothed disk mixer head for 3 minutes. The resultant powder was fine and free-flowing and remained stable after 5 months storage at ambient temperature.

Example 5

Cold tap water (47%), sucrose (50%) and CAB-O-SIL TS720 (3%) were mixed together in an IKA RE166 high speed mixer having a radial flow toothed disk mixer head for 3 minutes. The resultant powder was fine and free-flowing and remained stable beyond 5 days.

Example 6

Example 1 was repeated with the exception that sucrose was replaced with each of the following sugars: lactose, d-galactose, d-mannitol, maltose and d-raffinose. All sugars produced powders which were coarser and slightly wetter than those produced with sucrose.

Example 7

Golden syrup (97%) and CAB-O-SIL TS720 (3%) were mixed under low shear conditions at ambient temperature. The resultant powder was fine and free-flowing.

Example 8

Sodium chloride (5 g), cold tap water (31 g), granulated sugar (61 g) and CAB-O-SIL TS720 (3 g) were added to a 200 ml beaker and mixed in an IKA RE166 high shear mixer at 5000 rpm for 5 minutes. A dry free-flowing powder was obtained which remained physically stable after 5 days storage at ambient temperature.

Example 9

Cold tap water (30.6 g), granulated sugar (66 g), CAB-O-SIL TS720 (3 g) and a pesticide, the hydrophobic pyrethroid d-phenothrin (0.4 g), were added to a 200 ml beaker and mixed in an IKA RE166 high shear mixer at 5000 rpm for 5 minutes. A dry free-flowing powder was obtained with a bulk density of 0.71 g/ml. The powder remained physically stable with no loss of d-phenothrin after 12 months storage at ambient temperature.

Example 10

Adult houseflies, *Musca domestica*, when exposed to the powder formed in Example 9 were rapidly covered in particles of the powder. Total knockdown occurred within 2.5 minutes. In comparison, adult houseflies continually exposed to a deposit of the powder formed in Example 1 showed total knockdown after 6 hours.

Example 11

The composition described in Example 9 above was used to treat active wasp nests. A total of 13 active nests were treated. Three of these received a direct application of the composition to the inside of the nest. The remainder received indirect treatment by application of the composition either to the outer wall of the nest or to the access points in buildings where wasps were entering and subsequently reaching a hidden nest. Applications of the composition ranged from 75 g to 400 g per nest. The lower amounts were used for the direct applications into the nest whereas the higher amounts were used for the indirect applications where the location and size of the nests were unknown.

All treatments eradicated the wasps within 24 to 48 hours and caused no repellant or aggressive responses. In some applications, the wasps appeared to accept the treatment as food.

The species of wasps treated included the common wasp (*Vespula vulgaris*), the German wasp (*Vespula germanica*), the Norwegian wasp (*Dolichovespula norvegicus*) and the tree wasp (*Dolichovespula sylvestris*).

Example 12

Cold tap water (29.637 g), granulated sugar (66 g), Proxel GXL preservative (0.03 g), an oil-based ULV insecticide containing 3% pyrethrins/6% piperonyl butoxide/10% MGK264 (0.333 g) and CAB-O-SIL TS720 (4 g), were added to a 200 ml beaker and mixed with an IKA RE166 high shear mixer at 5,000 rpm for 5 minutes. A dry free-flowing powder was obtained with a bulk density of 0.65 g/ml. The powder remained physically stable after 9 months storage at ambient temperature. Adult houseflies, *Musca domestica*, when exposed to the powder were rapidly covered in particles of the powder. Total knockdown occurred within 10 minutes.

Example 13

Poultry red mites, *Dermanyssus gallinae*, when confined to the powder formed in Example 1 started to shrink in size after 15 minutes. Total mortality occurred within 2 hours.

Although not wishing to be bound by theory, this indicates that the silica absorbs or abrades the epicuticular layer that protects the mite from osmotic gradients. The high osmotic pressure of the sugar solution then affects rapid desiccation. The contribution of the silica is evident from poultry red mites exposed to icing sugar which survived visually unchanged for greater than 6 hours.

Example 14

Human lice, *Pediculus humanus corporis*, (body louse) were exposed to the powder formed in Example 1. The lice were provided with short lengths of human hair and gently massaged with the powder. Untreated control lice were similarly massaged but without the powder. Five replicates (10 lice per replicate) were employed for the treatment and for the untreated controls. Total mortality was achieved with the treatment by 24 hours. The mortality on the untreated control lice at 24 hours was a mean of 16%. This result against human lice is a good indicator for control against head lice *Pediculus humanus capitis*. The abdomen of treated lice appeared flattened indicating the same mode of action (i.e. desiccation) suggested from Example 13.

Example 15

The recipe described in Example 1 was mixed in a 250 ml beaker by an IKA RE166 high shear mixer at full speed (6,300 rpm). After 10 minutes mixing the product remained a free-flowing powder. By 15 minutes mixing this had transformed to a smooth, white, viscous cream. This cream (10 g) was easily massaged into human hair (grade 8 haircut) and readily washed off with clean water.

Example 16

Oil of cloves (0.5 g), cold tap water (30.5 g), granulated sugar (66 g) and CAB-O-SIL TS720 (3 g) were mixed in a 250 ml beaker by an IKA RE166 high shear mixer at 5,000 rpm for 3 minutes. A thick, white, viscous cream was formed with a typical odour of cloves. This cream (10 g) was easily massaged into human hair (grade 8 haircut) and readily washed off with clean water. No clove odour remained on the hair after washing.

Example 17

Difenacoum (an anticoagulant rodenticide) technical material, 98.9% purity, (0.1048 g), cold tap water (30.8952 g), granulated sugar (66 g) and CAB-O-SIL TS720 (3 g) were mixed in a 250 ml beaker by an IKA RE166 high shear mixer at 2,000 rpm for 5 minutes. A dry free-flowing powder was obtained with a bulk density of 0.71 g/ml. Chemical analysis showed a difenacoum content of 0.1041%. Direct pressure on this powder transformed it to a sticky, adhesive cream. Such a powder would be particularly suitable as a contact rodenticide.

The invention claimed is:

1. A particulate composition comprising from 40 to 80% by weight of sucrose, from 1.5 to 10% by weight of a finely particulate amorphous hydrophobic silica having a surface area in the range of from 80 to 300 $m^2/g$ and water which composition is in the form of fine particles of an aqueous solution of the sucrose, the surfaces of which fine particles of aqueous solution are coated with a coating of the finely particulate amorphous hydrophobic silica wherein the composition has biocidal activity.

2. A composition according to claim 1, wherein the finely particulate amorphous hydrophobic silica is present in an amount of from 2 to 3% by weight.

3. A composition according to claim 1, which additionally comprises a biocide.

4. A composition according to claim 3, wherein the biocide is selected from a rodenticide, an acaricide and an insecticide.

5. A process for producing a particulate composition which comprises the steps of mixing from 1.5 to 10% by weight of a finely particulate amorphous hydrophobic silica having a surface area in the range of from 80 to 300 $m^2/g$, from 40 to 80% by weight of sucrose and water whereby fine discrete particles of an aqueous solution of sucrose become coated on their surfaces by a coating of the amorphous hydrophobic silica.

6. A process according to claim 5, wherein mixing is carried out under high shear conditions.

7. A process according to claim 5, wherein the sucrose and the water are added to the finely particulate amorphous hydrophobic silica, prior to mixing, in the form of an aqueous solution of sucrose.

8. A process according to claim 5, wherein a biocide is also incorporated into the mixture.

9. A process according to claim 8, wherein the biocide is selected from a rodenticide, an acaricide and an insecticide.

10. A particulate composition comprising from 40 to 80% by weight a water-soluble saccharide, from 1.5 to 10% by weight of a finely particulate amorphous hydrophobic silica having a surface area in the range of from 80 to 300 $m^2/g$ and water wherein the source of the water-soluble saccharide and at least part of the water in the composition is an aqueous saccharide syrup, which composition is in the form of fine particles of an aqueous solution of the water-soluble saccharide, the surfaces of which fine particles of aqueous solution are coated with a coating of the finely particulate amorphous hydrophobic silica wherein the composition has biocidal activity.

11. A composition according to claim 10, wherein the aqueous saccharide syrup comprises a saccharide selected from dextrose, sucrose, d-galactose, d-mannitol, maltose and d-raffinose.

12. A composition according to claim 11, wherein the saccharide syrup comprises sucrose.

13. A composition according to claim 10, wherein the finely particulate amorphous hydrophobic silica is present in an amount of from 2 to 3% by weight.

14. A composition according to claim 10, which additionally comprises a biocide.

15. A composition according to claim 14, wherein the biocide is selected from a rodenticide, an acaricide and an insecticide.

16. A process for producing a particulate composition which comprises the steps of mixing from 1.5 to 10% by weight of a finely particulate amorphous hydrophobic silica having a surface area in the range of from 80 to 300 $m^2/g$, from 40 to 80% by weight of at least one water-soluble saccharide and water whereby fine discrete particles of an aqueous solution of the saccharide become coated on their surfaces by a coating of the amorphous hydrophobic silica particles, wherein the at least one water-soluble saccharide and at least part of the water are added to the finely particulate amorphous hydrophobic silica, prior to mixing, in the form of an aqueous saccharide syrup.

17. A process according to claim 16, wherein mixing is carried out under high shear conditions.

18. A process according to either claim 16, wherein the water-soluble saccharide comprises a saccharide selected from dextrose, sucrose, d-galactose, d-mannitol, maltose and d-raffinose.

19. A process according to claim 18, wherein the saccharide syrup comprises sucrose.

20. A process according to claim 16, wherein a biocide is also incorporated into the mixture.

21. A process according to claim 20, wherein the biocide is selected from a rodenticide, an acaricide and an insecticide.

22. A method for treating pests which comprises applying to a pest a particulate composition comprising from 40 to 80% by weight of a water-soluble saccharide, from 1.5 to 10% by weight of a finely particulate amorphous hydrophobic silica having a surface area in the range of from 80 to 300 $m^2/g$ and water which composition is in the form of fine particles of an aqueous solution of the water-soluble saccharide, the surfaces of which fine particles of aqueous solution are coated with a coating of the finely particulate amorphous hydrophobic silica.

23. The method according to claim 22, wherein the water-soluble saccharide is selected from dextrose, sucrose, d-galactose, d-mannitol, maltose and d-raffinose.

24. The method according to claim 22, wherein the water-soluble saccharide comprises a saccharide syrup.

25. The method according to claim 24, wherein the saccharide syrup comprises sucrose.

26. The method according to claim 22, wherein the finely particulate amorphous hydrophobic silica is present in the composition in an amount of from 2 to 3% by weight.

27. The method according to claim 22, wherein the composition additionally comprises a biocide.

28. The method according to claim 27, wherein the biocide is selected from a rodenticide, an acaricide and an insecticide.

* * * * *